United States Patent [19]

Kustra et al.

[11] Patent Number: 4,893,079

[45] Date of Patent: Jan. 9, 1990

[54] METHOD AND APPARATUS FOR CORRECTING EDDY CURRENT SIGNAL VOLTAGE FOR TEMPERATURE EFFECTS

[75] Inventors: Thomas A. Kustra, N. Huntingdon; Alfred J. Caffarel, Pittsburgh, both of Pa.

[73] Assignee: The United States of America as represented by the United States Department of Energy, Washington, D.C.

[21] Appl. No.: 237,203

[22] Filed: Aug. 29, 1988

[51] Int. Cl.[4] .................... G01N 27/72; G01B 7/10; G01R 33/12

[52] U.S. Cl. .................... 324/225; 324/230; 324/234

[58] Field of Search .............. 324/224, 225, 234, 236, 324/237, 238, 239, 240, 243, 229, 230, 231

[56] References Cited

U.S. PATENT DOCUMENTS

| | | | |
|---|---|---|---|
| 2,049,924 | 8/1936 | Pugh | 324/224 |
| 3,252,084 | 5/1966 | Krobath | 324/224 |
| 3,378,763 | 4/1968 | Hastings | 324/224 |
| 3,521,159 | 7/1970 | Morrow | 324/224 |
| 3,651,398 | 3/1972 | Urmenyi | 324/224 |
| 3,688,187 | 8/1972 | Loos | 324/224 |
| 4,567,435 | 1/1986 | Yamada et al. | 324/225 |

FOREIGN PATENT DOCUMENTS 2855912  6/1980  Fed. Rep. of Germany.
2308084 11/1976  France.

Primary Examiner—Gerard R. Strecker
Assistant Examiner—Walter E. Snow
Attorney, Agent, or Firm—William W. Randolph; William R. Moser; Richard E. Constant

[57] ABSTRACT

An apparatus and method for measuring physical characteristics of an electrically conductive material by the use of eddy-current techniques and compensating measurement errors caused by changes in temperature includes a switching arrangement connected between primary and reference coils of an eddy-current probe which allows the probe to be selectively connected between an eddy current output oscilloscope and a digital ohm-meter for measuring the resistances of the primary and reference coils substantially at the time of eddy current measurement. In this way, changes in resistance due to temperature effects can be completely taken into account in determining the true error in the eddy current measurement. The true error can consequently be converted into an equivalent eddy current measurement correction.

3 Claims, 4 Drawing Sheets

METHOD AND APPARATUS FOR CORRECTING EDDY CURRENT SIGNAL VOLTAGE FOR TEMPERATURE EFFECTS

The United States Government has rights in this invention pursuant to Contract No. DE-AC11-76PN00014 between the Department of Energy and Westinghouse Electric Corporation.

BACKGROUND OF THE INVENTION

This invention relates generally to electrical measurement apparatus, and more particularly to apparatus for measuring coating thicknesses of electrically-conductive materials by utilizing an induced eddy current method.

Eddy current methods are commonly used as a means of measuring coating thicknesses of certain materials. An example of such materials are Zircaloy samples that have been exposed to nuclear radiation, on which the thickness of a zirconium oxide corrosion film coating is to be measured utilizing the eddy current technique. The zirconium oxide coating thicknesses to be measured are usually less than $5 \times 10^{-4}$ inch, which requires extremely high accuracy in thickness measurement. However, temperature changes of the Zircaloy sample caused by gamma heating have a deleterious effect on accuracy. This is due to the fact that heat causes a change in the resistance of the probe coils used in obtaining the measurement which in turn produces an imbalance in an electrical bridge circuit employed to detect the eddy current value. Such temperature-caused resistance changes can result in measurement errors greater than 100%.

SUMMARY OF THE INVENTION

It is thus an object of the present invention to eliminate errors in an eddy current measurement apparatus.

It is a further object of the present invention to provide a method of determining temperature effects on an eddy current measurement apparatus by measuring resistance changes in the probe coils.

It is a still further object of the present invention to provide an apparatus for measuring physical characteristics of an electrically conductive material which is subject to temperature changes, which apparatus compensates for errors in the measurement of such characteristics due to the temperature changes.

The objects of the present invention are fulfilled by providing an apparatus for measuring the physical characteristics of an electrically conductive material, comprising eddy current probe means including a primary coil and a reference coil for producing an eddy current signal in response to said probe means coming in contact with said material, resistance measuring means for measuring the resistances of said primary coil and said reference coil, output means for outputting said eddy current signal, and switch means connected between said probe means, said measuring means, and said output means, for connecting said probe means to said measuring means to measure the resistance of said coils, and for connecting said probe means to said output means to obtain said eddy current signal, such that any error may be compensated for by correcting said eddy current signal in accordance with the measured resistances.

The objects of the present invention are also fulfilled by providing a method for compensating measurement errors in an eddy current measuring system comprising the steps of measuring the resistances of a primary coil and a reference coil of said system substantially at the moment of eddy current measurement, calculating the change in resistance differences between said primary and reference coils by determining the difference between the measured resistance differential and a nominal resistance differential, and correcting the value of eddy current measured by adjusting said value according to a predetermined relationship thereof with said change in resistance differential values.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF DRAWINGS

The present invention will become more fully understood from the detailed description given hereinbelow and accompanying drawings which are given by way of illustration only, and thus are not limitative of the present invention, and wherein:

FIGS. 6a–6e are examples for a particular eddy current probe of the relationship between coil resistance differences and eddy current output voltage.

DETAILED DESCRIPTION OF PREFERRED EMBODIMENTS

Figure 1:
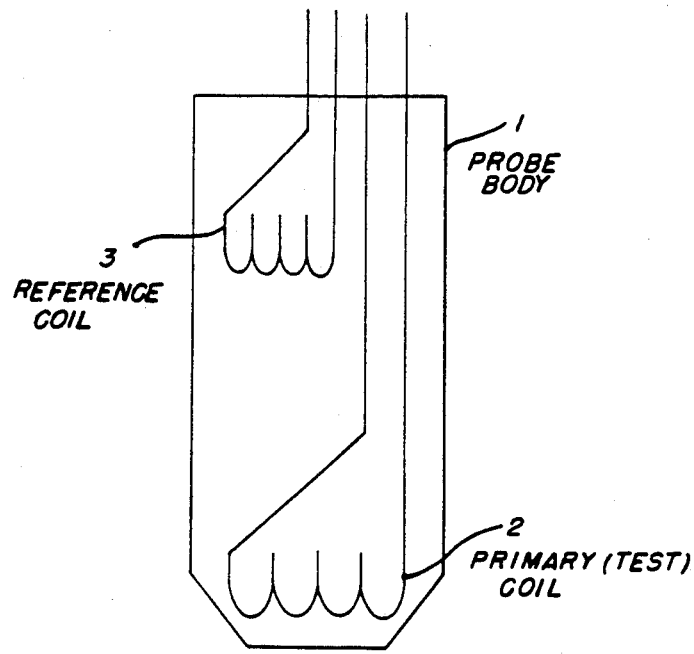
FIG. 1 is a plan view of an eddy current probe utilized in an eddy current measurement system.
Figure 2:
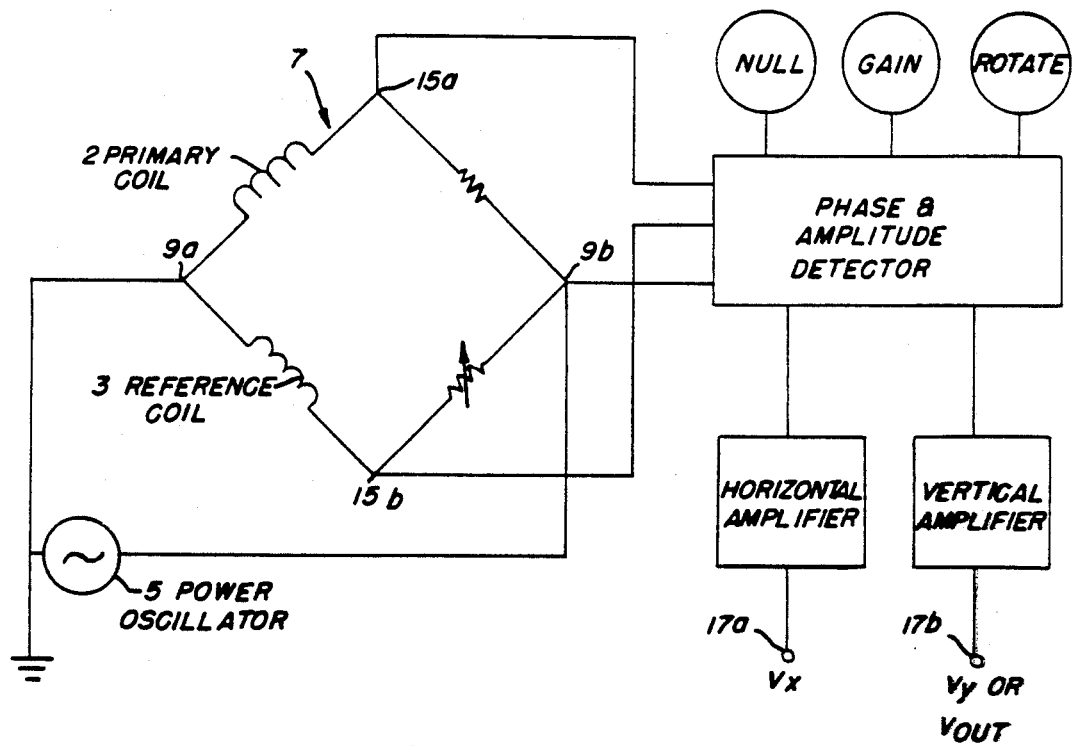
FIG. 2 is a schematic diagram of a bridge circuit containing the coils of the eddy current probe utilized in the eddy current measurement system and the detectors and amplifiers for outputting the eddy current signal.

FIG. 1 illustrates an eddy current probe utilized in an eddy current measurement system for measuring physical characteristics of materials such as coating thickness. Such a system comprises the eddy current probe 1 containing two coils. One coil is the primary or excitation coil 2 and the other is the reference coil 3. As shown in FIG. 2, the coils are electrically connected to a bridge circuit 7. A power oscillator 5 is connected to input terminals 9A and 9B of the bridge circuit, and an eddy current output signal is developed at output terminals 17A and 17B. The output is a signal with two voltage components, $V_x$ (or $V_{out}$) and $V_y$, which represents the relative difference in value between the complex impedance of the test coil and a reference coil.

Figure 3:
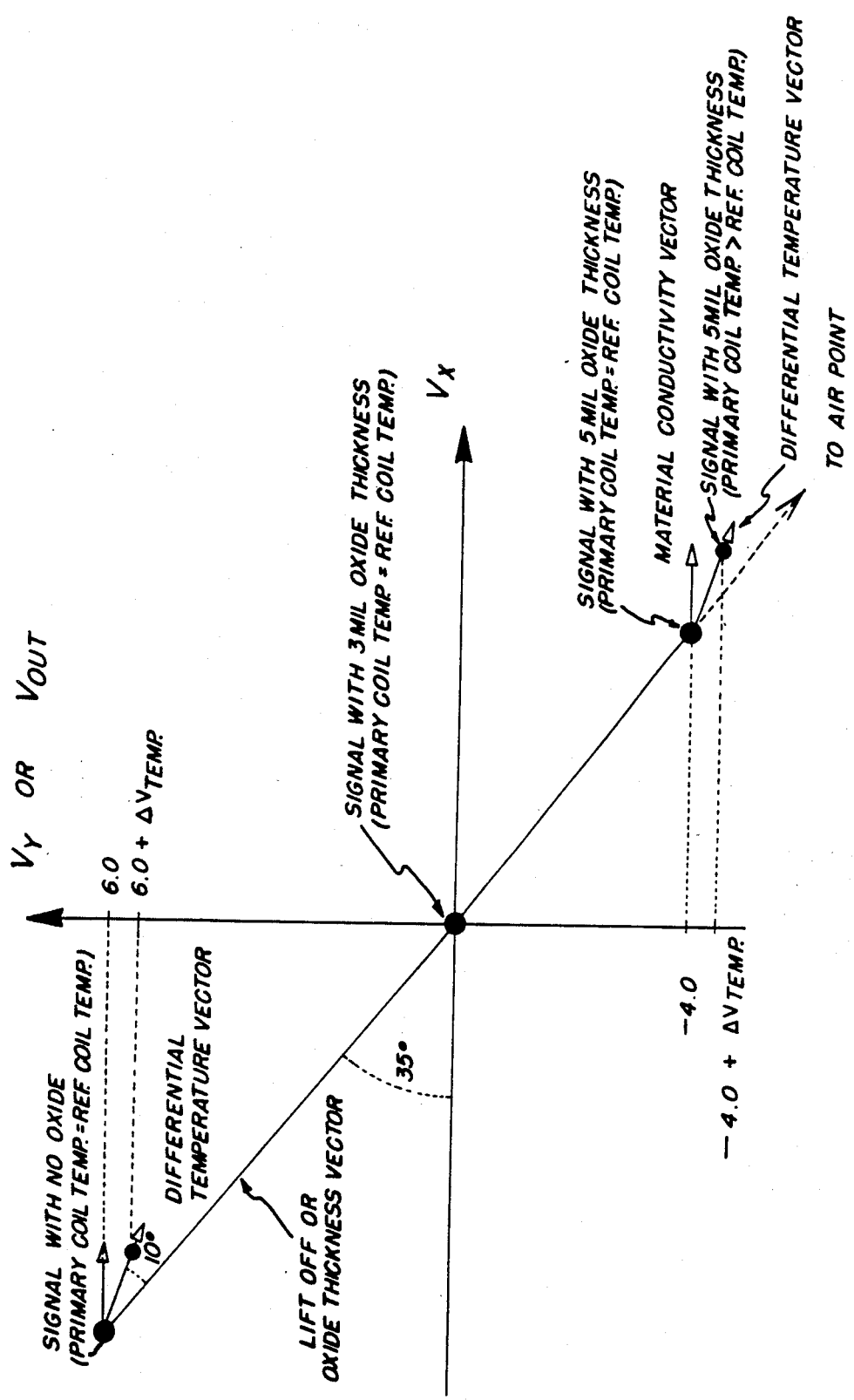
FIG. 3 is a preferred signal relationship to be established by calibration for the eddy current system.
Figure 4:
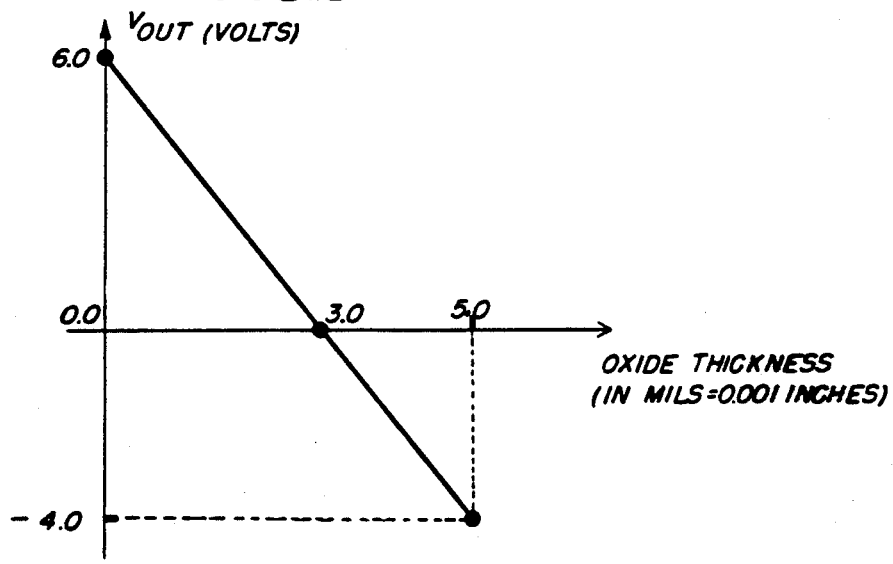
FIG. 4 is the relationship of the eddy current output voltage to oxide thickness for the preferred calibration shown in FIG. 3.

On taking coating thickness measurements, the system is first brought into balance by placing the probe 1 on a bare surface of material of the type which has the coating and nulling the instrument. Nulling is performed to prevent saturation of the signal amplifiers over the measurement range. The actual means for performing the nulling operation depends on the particular eddy current instrument being used. In some instruments, the bridge components are adjusted to balance the bridge and zero the output signal while other instruments zero the output by adding an opposing offset voltage. Nulling can be performed manually but many eddy current instruments provide an automatic nulling feature. If the probe is subsequently lifted from the surface, the system becomes unbalanced since the impedance of the coil is changed by the absence of the conductive material. The non-conducting coating exhibits effects similar to those resulting from the lifting of the probe from the surface in that it isolates the probe from the conductive surface. Such a phenomenon is known as "lift off". By calibrating the lift off, the coating thickness can be determined. Calibration consists of setting the null, offset, gain, and rotation controls of the eddy current oscilloscope to obtain a signal relationship similar to that shown in FIG. 3. When calibrated as in FIG. 3, the $V_y$ output, referred to as $V_{out}$, component of the signal is used for coating thickness measurements since changes in base material conductivity causes no change in $V_{out}$. FIG. 4 shows the relationship between $V_{out}$ and oxide thickness when calibrated in this way. However, temperature difference between the primary coil and reference coil results in a change in $V_{out}$ and therefore affects the thickness measurement. The magnitude of the change in signal output, referred to as $V_{TEMP}$ in FIG. 3, depends only on the temperature differential and is independent of the lift-off signal amplitude.

The resistivity of the coils is affected by temperature and thus changes in temperature cause changes in the balance of the system in addition to lift off. The coils can be affected by temperature changes not only by ambient or sample temperatures, but also by the length of time the eddy current probe remains in contact with the surface of the hot sample.

In order to directly measure the true temperature differential which affects the test, this invention provides a means to measure the resistance of the coils at approximately the same time as the thickness measurement is made.

Figure 5:
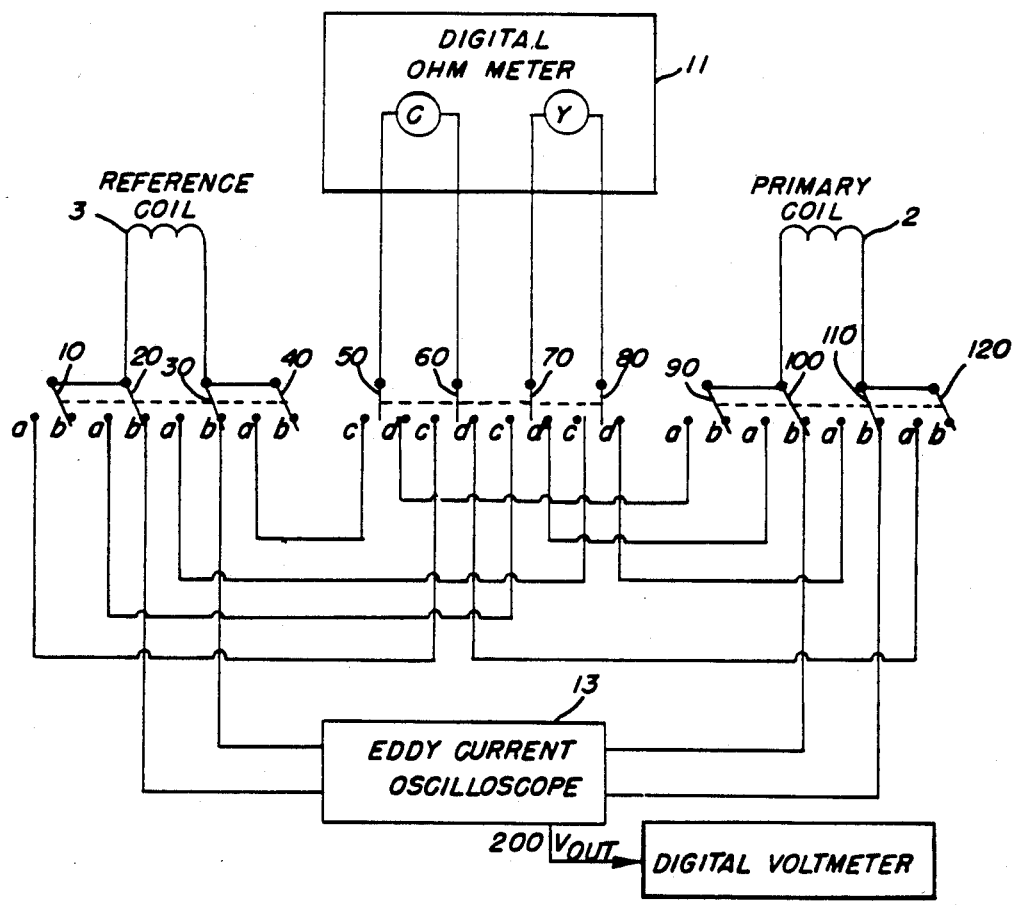
FIG. 5 is a schematic diagram of a switching arrangement of a preferred embodiment of the present invention.
Figure 6A:
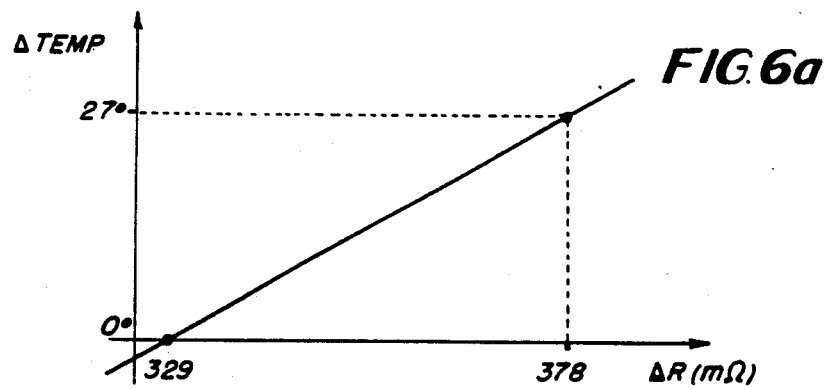
Figure 6B:
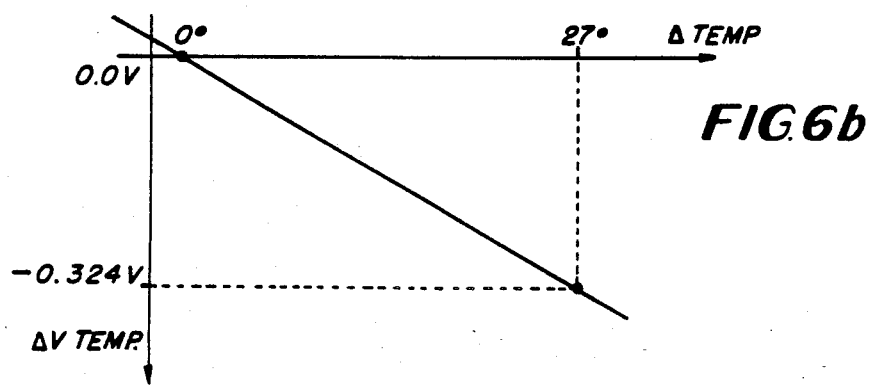
Figure 6C:
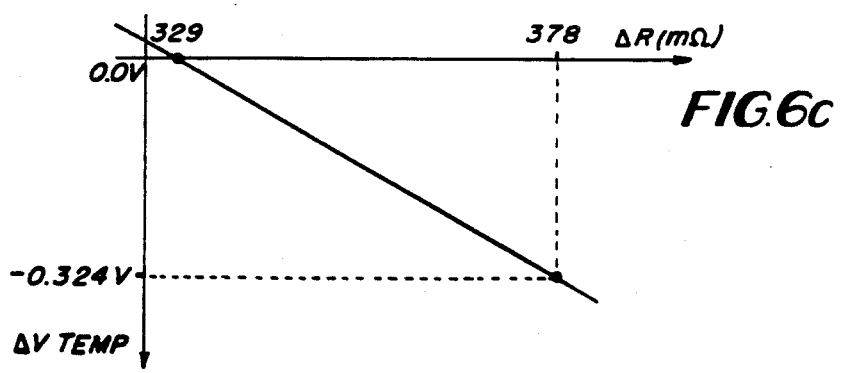

Referring now to FIG. 5, an embodiment of the present invention is shown, which includes a switching arrangement comprising a plurality of ganged switches 10 and 20, 30 and 40, 50 and 60, 70 and 80, 90 and 100, 110 and 120. These switches allow the selective connection between the primary coil 2 and reference coil 3 of the eddy current probe with an eddy current oscilloscope 13 and a digital ohm-meter 11. When the switches 10 to 40 of reference coil 3 and switches 90 to 120 of primary coil 2 are in the B position as shown, the eddy current measurement system is in a measurement mode wherein the coils are connected in circuit with the eddy current oscilloscope 13 and the output voltage at 200 is measured by a digital voltmeter 14. In this mode, switches 50 to 80 of ohm meter 11 are in a neutral position as shown. Immediately before or after taking an eddy current measurement, the resistances of coils 2 and 3 are measured by moving switches 10 to 40 and 90 to 120 to the A position. The resistance of reference coil 3 is measured by moving switches 50 to 80 of ohm meter 11 to the C terminals, and the resistance of primary coil 2 is measured by moving switches 50 to 80 to the D terminals. In this way, any deviation of the resistances of coils 2 and 3 as measured by ohm meter 11 from their nominal value can be related to an offset error due to temperature effects. The measured change in resistance difference between the primary coil 1 and the reference coil 2 can then be converted to an output voltage correction $V_{TEMP}$ from FIG. 6c which is subtracted from the measured eddy current output voltage 200. This temperature corrected voltage measurement can then be converted to an oxide thickness measurement using the FIG. 4 curve established by calibration at ambient temperature. The relationship between measured difference in coil resistance and output voltage in FIG. 6c is established by a combination of the data in FIGS. 6a and 6b. FIG. 6a shows the effect of temperature on the coil resistance and FIG. 6b shows the effect of temperature on the output voltage. The values used in the FIG. 6 curves are for one particular probe and must be established by measurement for each probe used.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for compensating measurement errors in an eddy current measuring system for measuring the thickness of coatings in heated environments comprising the steps of:

measuring the resistances of a primary coil and a reference coil of said system substantially at the moment of eddy current measurement by switching the primary and reference coils into a circuit with a digital ohm meter so that the eddy current measurements and the measured resistances are performed under the same temperature conditions;

calculating the change in resistance values of said primary and reference coils caused by the heated environment by determining the difference between the measured resistance of each coil in the heated environment and a nominal resistance for each coil; and correcting the value of the eddy current measured by adjusting the measured value according to a predetermined relationship thereof with said change in resistance values.

2. An apparatus for measuring physical characteristics of an electrically conductive material in a heated environment comprising:

eddy current probe means including a primary coil and a reference coil for producing an eddy current signal in response to said probe means coming in contact with said material;

resistance measuring means including a digital ohm meter for measuring the resistances of said primary coil and said reference coil;

output means for outputting said eddy current signal; and switch means connected between said probe means, said resistance measuring means, and said output means, for connecting said probe means to said resistance measuring means to measure the resistances of said coils, and for connecting said probe means to said output means to obtain said eddy current signal, said switch means connecting said probe means directly to said resistance measuring means and said output means so that said eddy current signal and said measured resistances are performed at substantially the same time and under the same conditions in the heated environment, wherein the resistance differential of the coils is proportional to temperature differential changes which cause errors in said eddy current signal produced by said probe means, such that said error may be compensated for by correcting the measured value of said eddy current signal in accordance with the measured resistances of the coils.

3. The apparatus of claim 2, wherein said output means comprises an eddy current oscilloscope and voltmeter.

* * * * *